(12) United States Patent
Acosta et al.

(10) Patent No.: US 8,288,323 B2
(45) Date of Patent: *Oct. 16, 2012

(54) COMPOSITIONS CONTAINING AMIDE SURFACTANTS AND METHODS FOR INHIBITING THE FORMATION OF HYDRATE AGGLOMERATES

(75) Inventors: Erick J. Acosta, Sugar Land, TX (US); Peter A. Webber, Sugar Land, TX (US)

(73) Assignee: Nalco Company, Naperville, IL (US)

( * ) Notice: Subject to any disclaimer, the term of this patent is extended or adjusted under 35 U.S.C. 154(b) by 452 days.

This patent is subject to a terminal disclaimer.

(21) Appl. No.: 12/396,076

(22) Filed: Mar. 2, 2009

(65) Prior Publication Data

US 2010/0222239 A1  Sep. 2, 2010

(51) Int. Cl.
C09K 8/52 (2006.01)
(52) U.S. Cl. ...................... 507/90; 166/305.1
(58) Field of Classification Search .................. 507/90; 166/305.1
See application file for complete search history.

(56) References Cited

U.S. PATENT DOCUMENTS

| | | | |
|---|---|---|---|
| 3,317,556 A | 5/1967 | Rose et al. |
| 3,894,962 A | 7/1975 | Allain |
| 4,652,623 A | 3/1987 | Chen et al. |
| 4,980,378 A | 12/1990 | Wong et al. |
| 6,319,971 B1 | 11/2001 | Kelland et al. |
| 6,702,946 B1 | 3/2004 | Huang et al. |
| 6,905,605 B2 | 6/2005 | Klump |
| 7,253,138 B2 | 8/2007 | Dahlmann et al. |
| 7,311,144 B2 | 12/2007 | Conrad |
| 7,408,004 B2 | 8/2008 | Struck et al. |
| 7,550,339 B2 | 6/2009 | Forbes |
| 2004/0164278 A1 | 8/2004 | Dahlmann et al. |
| 2005/0101495 A1 | 5/2005 | Dahlmann et al. |
| 2006/0094913 A1 | 5/2006 | Spratt |
| 2008/0113890 A1 | 5/2008 | Moreton et al. |
| 2010/0087338 A1 | 4/2010 | Acosta |

FOREIGN PATENT DOCUMENTS

| | | |
|---|---|---|
| GB | 962242 | 7/1964 |
| JP | 01038080 A * | 2/1989 |
| WO | 0240433 | 5/2002 |
| WO | 2004032824 | 4/2004 |
| WO | 2004041884 | 5/2004 |
| WO | 2004111161 | 12/2004 |
| WO | 2006051265 | 5/2006 |
| WO | 2008089262 | 7/2008 |

OTHER PUBLICATIONS

English Abstract of JP 01038080A.*
Sharma et al, "Green and mild protocol for hetero-Michael addition of sulfur and nitrogen nucleophiles in ionic liquid", Journal of Molecular Catalysis, A: Chemical, 277, pp. 215-220, 2007.
V. Fedi et al, Inseration of an Aspartic Acid Moiety into Cyclic Pseudopeptides: Synthesis and Biological Characterization of Potent Antagonists for the Human Tachykinin NK-2 Receptor, Journal of Medicinal Chemistry, vol. 47, pp. 6935-6947, 2004.
Billmeyer, F., Textbook of Polymer Science, John Wiley & Sons, Inc., 3rd edition, p. 5, 1984.
"Samarium (III) Triflate catalyzed conjugate addition of amines to electron-deficient alkenes" Yadav, J.S. et al., No. 22, pp. 3447-3450, 2007.

* cited by examiner

*Primary Examiner* — Alicia Toscano
(74) *Attorney, Agent, or Firm* — Edward O. Yonter; Andrew D. Sorenson

(57) ABSTRACT

One or more compositions and methods for inhibiting the formation of hydrate agglomerates in a fluid comprising water, gas, and optionally liquid hydrocarbon are disclosed. The fluid can be contained in an oil or gas pipeline or refinery.

21 Claims, No Drawings

COMPOSITIONS CONTAINING AMIDE SURFACTANTS AND METHODS FOR INHIBITING THE FORMATION OF HYDRATE AGGLOMERATES

FIELD OF THE INVENTION

This invention pertains to one or more compositions and methods for inhibiting the formation of hydrate agglomerates in a fluid comprising water, gas, and optionally liquid hydrocarbon, e.g. a fluid in an oil or gas pipeline or refinery.

BACKGROUND OF THE INVENTION

Since Hammerschmidt discovered in 1934 that gas hydrates block gas pipelines, research for the prevention of hydrate formation and agglomeration has become an important matter. Gas hydrates can be easily formed during the transportation of oil and gas in pipelines when the appropriate conditions are present. Water content, low temperatures, and elevated pressure are required for the formation of gas hydrates. The formation of gas hydrates often results in lost oil production, pipeline damage, and safety hazards to field workers.

There are two approaches to prevent or slowdown the formation of gas hydrates, thermodynamic inhibitors and low dosage hydrate inhibitors (LDHIs). Thermodynamic inhibitors are substances that can reduce the temperature at which the hydrates form at a given pressure and water content. Methanol and ethylene glycol are among the most common thermodynamic inhibitors used in the oil industry. Although thermodynamic inhibitors are quite effective, they require large doses to achieve high concentration in the water phase. Thermodynamic inhibitors are regularly dosed at concentrations as high as 50% based on water content during oil and gas production. Therefore, there is a substantial cost associated with the transportation and storage of large quantities of these solvents. A more cost-effective alternative is the use of LDHIs, as they generally require less than a 2% dose based on water content to inhibit the nucleation or growth of gas hydrates. There are two general types of LDHI, kinetic hydrate inhibitors (KHIs) and anti-agglomerants (AAs/AA). KHIs work by delaying the growth of gas hydrate crystals as anti-nucleators. AAs allow the hydrates to form but then prevent them from agglomerating and accumulating into larger masses capable of causing plugs in oil and gas pipelines. An AA enables gas hydrates to form but in the shape of a fluid slurry dispersed in the liquid hydrocarbon phase. In general, the water cut should be below 50% because otherwise the slurry becomes too viscous to transport.

There is an ongoing need for new and effective methods of inhibiting the formation of hydrate agglomerates, particularly those that are capable of operating under higher water-cuts.

SUMMARY OF THE INVENTION

The invention pertains to compositions, e.g. anti-agglomerants, as well as methods for inhibiting the formation of hydrate agglomerates in a fluid comprising water, gas, and optionally liquid hydrocarbon.

In one aspect, the present invention provides for a composition comprising the following formula and optionally salts thereof:

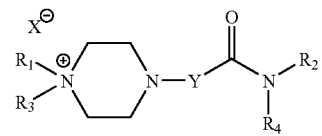

where $R_1$ is $C_nH_{2n+1}$, wherein n=0 to 12; benzyl; or H;
where $R_2$ is a $C_4$ to $C_{22}$ alkyl;
where $R_3$ is $C_nH_{2n+1}$, wherein n=0 to 12; benzyl; or H;
where $R_4$ is $C_nH_{2n+1}$, wherein n=0 to 22; or H
where $X^-$ is an anion, halogen, a carboxylate, or a sulfate and wherein $X^-$ is only present when both $R_1$ and $R_3$ are present;
where $Y=(CH_2)_n$, wherein n=1 to 8; and
wherein $R_3$ and $R_1$ can not be hydrogen or n=0 at the same time.

In another aspect, the present invention provides for a method of inhibiting the formation of hydrate agglomerates in a fluid comprising water, gas, and optionally liquid hydrocarbon comprising adding to the fluid an effective amount of a composition comprising the following formula and optionally salts thereof:

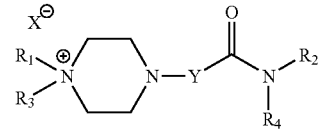

where $R_1$ is $C_nH_{2n+1}$, wherein n=0 to 12; benzyl; or H;
where $R_2$ is a $C_4$-$C_{22}$ alkyl;
where $R_3$ is $C_nH_{2n+1}$, wherein n=0 to 12; benzyl; or H;
where $R_4$ is $C_nH_{2n+1}$, wherein n=0 to 22; or H
where $X^-$ is an anion, halogen, a carboxylate, or a sulfate and wherein $X^-$ is only present when both $R_1$ and $R_3$ are present;
where $Y=(CH_2)_n$, wherein n=1 to 8; and
wherein $R_3$ and $R_1$ can not be hydrogen or n=0 at the same time.

DETAILED DESCRIPTION OF THE INVENTION

A. Compositions

As stated above, the compositions contain a generic formula.

In one embodiment, the compositions contain various amounts of different compositions that fall within the claimed formula.

In another embodiment, the alkyl groups of $R_1$ and/or $R_2$ and/or $R_4$ are linear, branched, cyclic, and/or unsaturated.

In another embodiment, $R_3$ is a methyl or ethyl group. When possible the alkyl groups can be linear or branched.

In another embodiment, the halogen is chlorine, bromine, or iodine. The halogen is in ionic form when it is associated with the composition.

In another embodiment, $Y=(CH_2)_n$, wherein n=1 to 4. When possible, Y is linear or branched.

In another embodiment, $R_1$ is a $C_4$-$C_8$ alkyl.
In another embodiment, $R_2$ is a $C_6$-$C_{18}$ alkyl.
In another embodiment, the composition contains the following formula and optionally salts thereof:

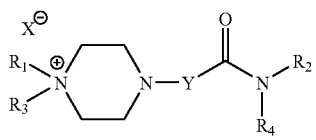

where $R_1$ is $C_4H_9$, $C_6H_{13}$, $C_8H_{17}$, or benzyl;
where $R_2$ is a $C_8H_{17}$, $C_{12}H_{25}$, or $C_{18}H_{35}$;
where $R_3$ is $CH_3$ or $C_2H_5$;
where $R_4$ is $C_nH_{2n+1}$, wherein n=0 to 22; or H
where $X^-$ is an anion, halogen, a carboxylate, or a sulfate and wherein $X^-$ is only present when both $R_1$ and $R_3$ are present;
where $Y=(CH_2)_n$, wherein n=1 to 8; and
wherein $R_3$ and $R_1$ can not be hydrogen or n=0 at the same time.

In a further embodiment, $Y=(CH_2)_n$, wherein n=1 to 2.

In another embodiment, the composition contains the following formula and optionally salts thereof:

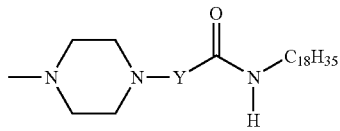

In another embodiment, the composition contains the following formula:

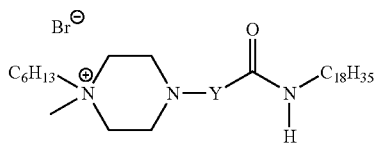

Various synthetic methodologies, which can be appreciated by one of ordinary skill in the art, can be utilized to make the claimed compositions.

In one embodiment, a composition is produced by reacting an alkyl acrylate with 1-methylpiperazine and then subsequently reacting the resulting product with an amine to form an amide and reacting said amide with an alkyl halide.

In a further embodiment, the amine is oleylamine.

In a further embodiment, the alkyl halide is 1-bromohexane.

The compositions of this invention can contain one or more additional chemistries. Various formulations can be appreciated by one of ordinary skill in the art and can be made without undue experimentation.

In one embodiment, the composition further comprises one or more hydrate inhibitors.

In another embodiment, the composition further comprises one or more thermodynamic hydrate inhibitors, one or more kinetic hydrate inhibitors, one or more anti-agglomerants, or a combination thereof.

In another embodiment, the composition further comprises one or more asphaltene inhibitors, paraffin inhibitors, corrosion inhibitors, scale inhibitors, emulsifiers, water clarifiers, dispersants, emulsion breakers, or a combination thereof.

In another embodiment, the composition further comprises one or more polar or nonpolar solvents or a mixture thereof.

In another embodiment, the composition further comprises one or more solvents selected from isopropanol, methanol, ethanol, heavy aromatic naptha, toluene, ethylene glycol, ethylene glycol monobutyl ether (EGMBE), diethylene glycol monoethyl ether, xylene, kerosene, diesel, isobutanol, heptane, or a combination thereof.

B. Methods

As stated above, the present invention provides for a method of inhibiting the formation of hydrate agglomerates in a fluid comprising water, gas, and optionally liquid hydrocarbon comprising adding to the fluid an effective amount of a composition comprising the following formula and optionally salts thereof:

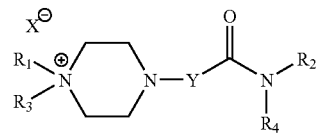

where $R_1$ is $C_nH_{2n+1}$, wherein n=0 to 12; benzyl; or H;
where $R_2$ is a $C_4$ to $C_{22}$ alkyl;
where $R_3$ is $C_nH_{2n+1}$, wherein n=0 to 12; benzyl; or H;
where $R_4$ is $C_nH_{2n+1}$, wherein n=0 to 22; or H
where $X^-$ is an anion, halogen, a carboxylate, or a sulfate and wherein $X^-$ is only present when both $R_1$ and $R_3$ are present;
where $Y=(CH_2)_n$, wherein n=1 to 8; and
wherein $R_3$ and $R_1$ can not be hydrogen or n=0 at the same time.

In one embodiment, the compositions contain various amounts of different compositions that fall within the claimed formula.

In another embodiment, the alkyl groups of $R_1$ and/or $R_2$ and/or $R_4$ are linear, branched, cyclic, and/or unsaturated.

In another embodiment, $R_3$ is a methyl or ethyl group. When possible the alkyl groups can be linear or branched.

In another embodiment, the halogen is chlorine, bromine, or iodine. The halogen is in ionic form when it is associated with the composition.

In another embodiment, $Y=(CH_2)_n$, wherein n=1 to 4. When possible, Y is linear or branched.

In another embodiment, $R_1$ is a $C_4$-$C_8$ alkyl.

In another embodiment, $R_2$ is a $C_6$-$C_{18}$ alkyl

In another embodiment, the composition contains the following formula and optionally salts thereof:

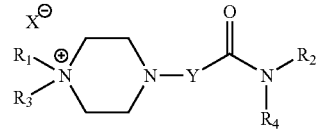

where $R_1$ is $C_4H_9$, $C_6H_{13}$, $C_8H_{17}$, or benzyl;
where $R_2$ is a $C_8H_{17}$, $C_{12}H_{25}$, or $C_{18}H_{35}$;
where $R_3$ is $CH_3$ or $C_2H_5$;
where $R_4$ is $C_nH_{2n+1}$, wherein n=0 to 22; or H
where $X^-$ is an anion, halogen, a carboxylate, or a sulfate and wherein $X^-$ is only present when both $R_1$ and $R_3$ are present;
where $Y=(CH_2)_n$, wherein n=1 to 8; and
wherein $R_3$ and $R_1$ can not be hydrogen or n=0 at the same time.

In a further embodiment, Y=(CH$_2$)$_n$, wherein n=1 to 2.

In another embodiment, the composition contains the following formula and optionally salts thereof:

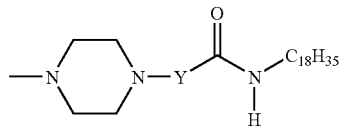

In another embodiment, the composition contains the following formula:

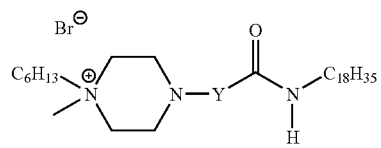

The composition is applied to a fluid that contains various levels of salinity.

In one embodiment, the fluid has a salinity of 1 to 20 weight/weight (w/w) total dissolved solids (TDS).

The composition is applied to a fluid that contains various levels of water cut. One of ordinary skill in the art would interpret water cut to mean the percentage (%) of water in a composition containing an oil and water mixture.

In one embodiment, the water cut is from greater than 0% to 100% volume/volume (v/v).

In another embodiment, the water cut is from 1 to 60 volume/volume (v/v) percent.

Various synthetic methodologies, which can be appreciated by one of ordinary skill in the art, can be utilized to make the claimed compositions. These compositions are then utilized in methods of inhibiting the formation of hydrate agglomerates.

In one embodiment, a composition is produced by reacting an alkyl acrylate with 1-methylpiperazine and then subsequently reacting the resulting product with an amine to form an amide and reacting said amide with an alkyl halide.

In a further embodiment, the amine is oleylamine.

In a further embodiment, the alkyl halide is 1-bromohexane.

The compositions of this invention can contain one or more additional chemistries. Various formulations can be appreciated by one of ordinary skill in the art and can be made without undue experimentation.

In one embodiment, the composition further comprises one or more hydrate inhibitors.

In another embodiment, the composition further comprises one or more thermodynamic hydrate inhibitors, one or more kinetic hydrate inhibitors, one or more anti-agglomerants, or a combination thereof.

In another embodiment, the composition further comprises one or more asphaltene inhibitors, paraffin inhibitors, corrosion inhibitors, scale inhibitors, emulsifiers, water clarifiers, dispersants, emulsion breakers, or a combination thereof.

In another embodiment, the composition further comprises one or more polar or nonpolar solvents or a mixture thereof.

In another embodiment, the composition further comprises one or more solvents selected isopropanol, methanol, ethanol, heavy aromatic naptha, toluene, ethylene glycol, ethylene glycol monobutyl ether (EGMBE), diethylene glycol monoethyl ether, xylene, kerosene, diesel, isobutanol, heptane, or a combination thereof.

The fluid in which the compositions and/or formulations are applied to can be contained in many different types of apparatuses, especially those that transport a fluid from one point to another point, e.g. in one embodiment, the fluid is contained in an oil and/or gas pipeline.

In another embodiment, the fluid is contained in refineries, e.g. separation vessels, dehydration units, gas lines, and pipelines.

The compositions of the present disclosure and/or formulations thereof can be applied to a fluid in various ways that would be appreciated by of ordinary skill in the art. One of ordinary skill in the art would appreciate these techniques and the various locations to which the compositions or chemistries can be applied.

In one embodiment, the compositions and/or formulations are pumped into the oil/gas pipeline by using an umbilical line. In a her embodiment, capillary injection systems can be utilized to deliver the surfactants, in this case anti-agglomerants. U.S. Pat. No. 7,311,144 provides a description of an apparatus and methods relating to capillary injection, which is herein incorporated by reference.

Various dosage amounts of a composition and/or formulation can be applied to the fluid to inhibit the formation of hydrate agglomerates. One of ordinary skill in the art would be able to calculate the amount of anti-agglomerant for a given situation, e.g. content of aqueous medium could be a factor, without undue experimentation.

In one embodiment, the dose range for the anti-agglomerant that is applied to an aqueous medium, e.g. aqueous medium contained in an oil/gas pipeline, is between 0.1% volume to 2% volume based on water cut.

The methodologies described in the present invention may be utilized with other compositions that are commensurate in scope with this application's disclosure. Other chemistries used for inhibiting the formation of agglomerants in fluids, which are outside the specific generic formula described above, but are commensurate in scope with the claimed compositions generic formula, may be utilized if the system conditions permit the compositions to inhibit the formation of agglomerants (hydrate agglomerates); this protocol can be achieved without undue experimentation, specifically, e.g. the rocking test described below can be utilized in determining whether a chemistry works or not.

EXAMPLES

I. Synthesis of Compositions/AA Chemicals

General Procedure/Scheme:

The present invention relates to the synthesis and use of beta-amino amide surfactants as anti-agglomeration chemicals. These surfactants present piperazine groups as the hydrophilic portion of the molecule and a fatty alkyl group as hydrophobes. Scheme 1 shows the generic synthetic procedure for the preparation for the beta-amino amide compounds. The first step of the reaction involves a Michael Addition reaction between an N-alkyl piperazine and methyl acrylate to make compound I (Structure I). Then compound I is reacted with an alkyl amine to form the amide adduct II (Structure II) and releases methanol as a by-product. The last step of the synthesis requires the reaction of an alkyl halide with compound II to form surfactant III (Structure III).

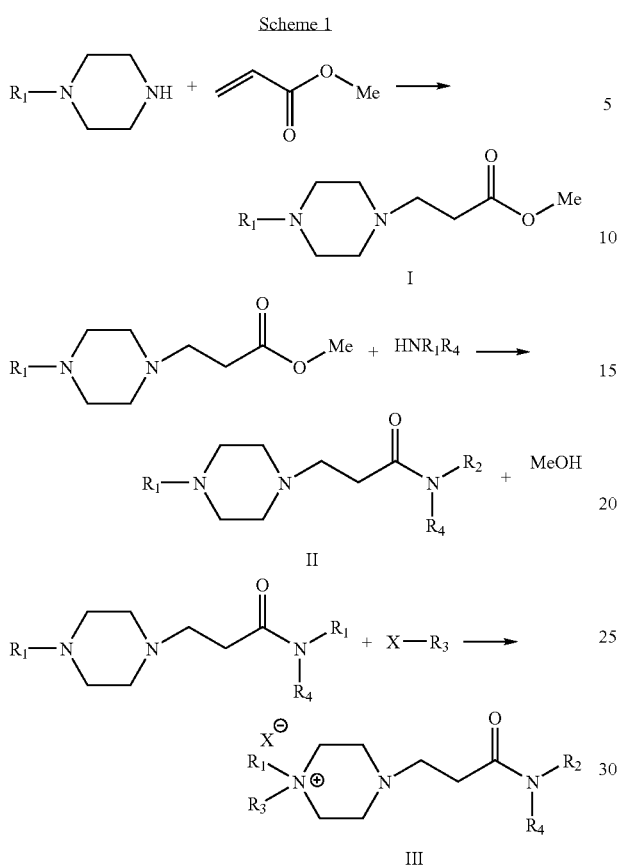

Representative Synthetic Procedure:

A. Synthesis of methyl 3-(4-methylpiperazin-1-yl)propanoate

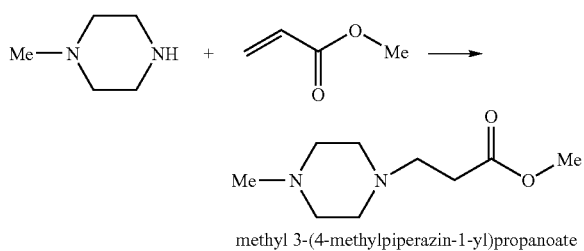

methyl 3-(4-methylpiperazin-1-yl)propanoate

In a 500-mL 3-neck round bottom flask, 150.0 g (1.7 moles) of methyl acrylate is charged. The reactor is cooled to 0° C. using an ice bath. Then, 77.0 g (0.77 moles) of 1-methyl piperazine are added slowly to prevent overheating of the reaction mass. The temperature should be maintained below 50° C. by controlling the addition rate of 1-methyl piperazine. Overheating may cause polymerization of the excess methyl acrylate present in the reactor. Once the addition is completed, the mixture is agitated using a magnetic stirring bar and the temperature adjusted to 50° C. for at least 16 hours. Then, the reaction is allowed to cool to ambient temperature and the excess methyl acrylate is removed under vacuum. The final product is a light brown liquid at ambient temperature. The transformation is monitored with thin layer chromatog- raphy (TLC) using 9:1 $CHCl_3$/MeOH. Complete conversion is apparent from the lack of olefinic protons in the $^1$H-NMR spectra. $^1$H-NMR (300 MHz, $CDCl_3$): δ 3.20 (s, 3H), 2.12 (t, 7.3 Hz, 2H), 1.94 (m, 10H), 1.71 (s, 3H). $^{13}$C-NMR (75 MHz, $CDCl_3$): δ 171.31, 54.00, 52.41, 51.78, 50.22, 44.92, 30.96.

B. Synthesis of N-dodecyl-3-(4-methylpiperazin-1-yl)propanamide

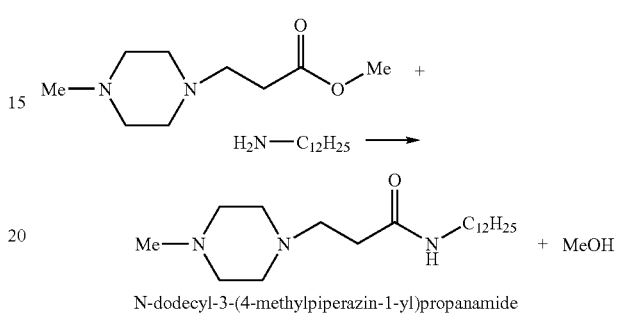

N-dodecyl-3-(4-methylpiperazin-1-yl)propanamide

Methyl 3-(4-methylpiperazin-1-yl)propanoate 40.0 g (0.21 moles) and dodecylamine 39.7 g (0.21 moles) are charged into a 3-neck 250-mL round bottom flask equipped with a Dean-Stark trap, thermocouple, and reflux condenser. The mixture is agitated using a magnetic stirring bar and heated to 185° C. for five hours. The volume of methanol that is distilled from the reaction is used to monitor the progress of the reaction. Evidence of the chemical transformation is observed by thin layer chromatography (TLC) analysis using a 4:1 $CHCl_3$/MeOH as mobile phase. The final product is a light yellow solid at ambient temperature. $^1$H-NMR (300 MHz, CDCl3): δ 2.98 (m, 2H), 2.07 (m, 15H), 1.27 (m, 2H), 1.0 (m, 18H), 0.65 (t, 6.7 Hz, 3H). $^{13}$C-NMR (75 MHz, CDCl3): δ 171.70, 54.60, 54.39, 54.34, 53.45, 51.86, 45.39, 38.45, 31.60, 31.38, 29.14, 29.11, 28.93, 28.85, 28.83, 26.65, 22.15, 13.61.

C. Synthesis of 4-(3-(dodecylamino)-3-oxopropyl)- 1-hexyl-1-methylpiperazin-1-ium bromide

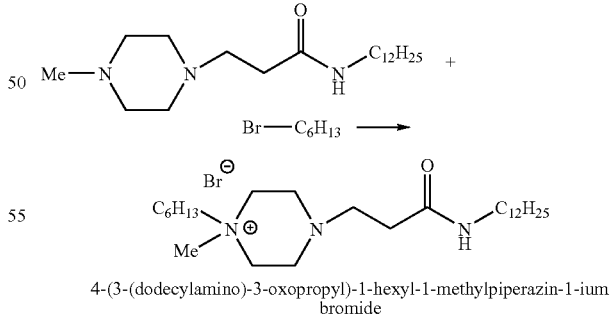

4-(3-(dodecylamino)-3-oxopropyl)-1-hexyl-1-methylpiperazin-1-ium bromide

N-dodecyl-3-(4-methylpiperazin-1-yl)propanamide 30.0 g (0.088 moles), 1-bromohexane 14.6 g (0.088 moles), and 11.2 g of isopropyl alcohol are charged into a 3-neck 250-mL round bottom flask equipped with a thermocouple, and reflux condenser. The mixture is agitated using a magnetic stirring bar and heated to reflux overnight. Then, the reaction mass is cooled down to about 40° C. and diluted to 40% active solids with 56 g of methanol. Evidence of the chemical transformation is observed by TLC analysis using a 4:1 CHCl$_3$/MeOH as mobile phase. The final product is a light brown solution at ambient temperature. $^1$H-NMR (300 MHz, CDCl3): δ 3.10 (m, 5H), 2.90 (m, 10H), 2.36 (m, 4H), 1.34 (bs, 2H), 0.80 (m, 26H), 0.44 (m, 6H). $^{13}$C-NMR (75 MHz, CDCl3): δ 170.94, 62.39, 59.24, 52.17, 48.35, 45.12, 38.39, 32.50, 30.75, 30.12, 28.52, 28.49, 28.38, 28.18, 28.18, 25.98, 24.85, 24.11, 21.50, 21.28, 20.74, 12.92, 12.74.

D. Testing Samples

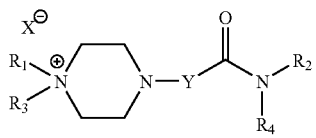

TABLE 1

Sample description

| Example | R$_2$ | R$_1$ | R$_3$ | X |
|---|---|---|---|---|
| Blank | N/A | N/A | N/A | N/A |
| Comparative Example A | N/A | N/A | N/A | N/A |
| Comparative Example B | N/A | N/A | N/A | N/A |
| 1 | —C$_8$H$_{17}$ | None | —CH$_3$ | None |
| 2 | —C$_{12}$H$_{25}$ | None | —CH$_3$ | None |
| 3 | —(CH$_2$)$_8$CH=CH(CH$_2$)$_8$—H [cis isomer] | None | —CH$_3$ | None |
| 4 | —CH(CH$_3$)(CH$_2$)$_5$—H | None | —CH$_3$ | None |
| 5 | —CH$_2$CH(CH$_2$CH$_3$)(CH$_2$)$_4$—H | None | —CH$_3$ | None |
| 6 | —C$_8$H$_{17}$ | Benzyl | —CH$_3$ | Cl |
| 7 | —C$_{12}$H$_{25}$ | Benzyl | —CH$_3$ | Cl |
| 8 | —(CH$_2$)$_8$CH=CH(CH$_2$)$_8$—H [cis isomer] | Benzyl | —CH$_3$ | Cl |
| 9 | —CH(CH$_3$)(CH$_2$)$_5$—H | Benzyl | —CH$_3$ | Cl |
| 10 | —CH$_2$CH(CH$_2$CH$_3$)(CH$_2$)$_4$—H | Benzyl | —CH$_3$ | Cl |
| 11 | —C$_8$H$_{17}$ | n-Butyl | —CH$_3$ | Br |
| 12 | —C$_{12}$H$_{25}$ | n-Butyl | —CH$_3$ | Br |
| 13 | —(CH$_2$)$_8$CH=CH(CH$_2$)$_8$—H [cis isomer] | n-Butyl | —CH$_3$ | Br |
| 14 | —CH(CH$_3$)(CH$_2$)$_5$—H | n-Butyl | —CH$_3$ | Br |
| 15 | —CH$_2$CH(CH$_2$CH$_3$)(CH$_2$)$_4$—H | n-Butyl | —CH$_3$ | Br |
| 16 | —C$_8$H$_{17}$ | n-Hexyl | —CH$_3$ | Br |
| 17 | —C$_{12}$H$_{25}$ | n-Hexyl | —CH$_3$ | Br |
| 18 | —(CH$_2$)$_8$CH=CH(CH$_2$)$_8$—H [cis isomer] | n-Hexyl | —CH$_3$ | Br |
| 19 | —CH(CH$_3$)(CH$_2$)$_5$—H | n-Hexyl | —CH$_3$ | Br |
| 20 | —CH$_2$CH(CH$_2$CH$_3$)(CH$_2$)$_4$—H | n-Hexyl | —CH$_3$ | Br |

II. Anti-Agglomerate (AA) Testing

A. Rocking Cell Procedure for Anti-Agglomeration Testing on Magnolia Crude Oil

A rocking cell has two parts, a manifold and a cell body. The manifold is made up of stainless steel fittings that are welded together. It has three stems. An inlet stem is used to charge gas into the cell. An outlet stem is used to release the gas out of the cell. The third stem connects to a transducer, which measures the pressure inside of the cell. The cell body has three layers. The outer layer is a polycarbonate tube, with a thickness that is 0.7 cm. The middle layer is made of stainless steel metal and is connected to the manifold. The inner layer contains a high-pressure sapphire tube, which has an outer diameter of 2.8 cm, an inner diameter that of 1.85 cm, and a length of 5 cm. This sapphire tube can handle pressure up to 3000 psi. A stainless steel ball, which of 1.6 cm diameter is located inside a sapphire tube to induce turbulence and mix the fluids during the rocking process.

The fluid usually contains three different components. For this Anti-Agglomerate test, 7.2 mL of warm magnolia crude oil is first injected into the cell. Next, 4.8 mL of a solution containing 7% by weight of NaCl in DI water was injected into the cell to make a 40% water cut mixture. AA chemicals are then put into the cell. The dosage of the AA chemical is based on the amount of aqueous phase. The initial condition for the test had a temperature of 21° C. Each cell is charged by Green Canyon gas and pressurized up to 2500 psi. The cells were rocked for at least 1.5 to 2 hours until the fluid was saturated and the pressure became stable; then the temperature was set at 4° C. The rocking sequence was the following: cells were rocked for 16 hours (simulating steady state flowing); stayed static for 6 hours; and then rocked back for 2 hours. Pressure data was recorded during this time. Observations were taken every two or three hours before the rocking was stopped and right after the start up of the rocking test.

The AAs utilized above were diluted in methanol to a final concentration of 60% actives. The only exception is comparative example B that has a concentration of 40% actives in methanol. The solutions are then dosed to obtain a final concentration of 0.6% vol. of AA (based upon actives) in the aqueous phase. For example, a typical experiment at 40% water cut and a total volume of 12 mL will require 4.8 mL of brine, 7.2 mL of oil, and 29 μL of surfactant solution. The mixture is charged into the rocking cell, as described above, and a stainless steel ball is added to promote mixing during the rocking part of the experiment.

The performance of the hydrate inhibitor is ranked from 1 (the worst performer) to 5 (the best) based on the following criteria:

| | | LDHI Rating System |
|---|---|---|
| Rating | Test result | Observations |
| 1 | Fail | The rolling ball is stuck and/or the liquid level has dropped below an observable amount. |
| 2 | Fail | Large to medium agglomerates are present and/or the liquid level has dropped significantly. There is significant resistance to the rolling of the ball in the cell. |
| 3 | Marginal pass | Medium agglomerates are formed in the viewable area and/or the liquid level has dropped moderately. There is some resistance to the rolling ball in the cell. |
| 4 | Pass | Small agglomerates are formed and/or the liquid level has dropped slightly, but the solution is free flowing without hindrance. |
| 5 | Pass | Tiny and well-dispersed hydrates in the hydrocarbon phase, high liquid level, and free-flowing without hinderance. |

B. Anti-Agglomeration Results

The function of AA chemicals is to disperse hydrate particles in the oil phase while preventing them from coagulating and causing plugs. Since the hydrates are dispersed in the oil phase, as the water cut increases it becomes more difficult to achieve anti-agglomeration performance.

The AAs are diluted in methanol to a final concentration of either 40% or 60% actives. The solutions are then dosed to obtain a final concentration of 0.6% vol. of AA (based upon actives) in the aqueous phase. For example, a typical experiment at 40% water cut and a total volume of 12 mL will require 4.8 mL of brine, 7.2 mL of oil, and 29 µL of surfactant (AA containing) solution. The mixture is charged into the rocking cell and a stainless steel ball is then added to promote mixing during the rocking part of the experiment. Then, the cells are placed inside a temperature-controlled tank at 21° C. and pressurized to 2500 psi with methane gas. The temperature of the rocking cell tank is gradually adjusted to 4° C. while rocking. The cells are rocked for 16 hours (simulating steady-state flowing) followed by a 6-hour shut-in, then 2 more hours of rocking.

The table below shows water cut data. Examples 1 to 5 are non-quaternary surfactants of Structure II that contain different alkyl amides as the hydrophobic group. These materials are the intermediates for the preparation of the quaternary ammonium surfactants of Structure III. They were evaluated for anti-agglomeration performance and only example 3, which contains an oleyl amide group, demonstrated anti-agglomeration performance at 40% water cut. Examples 6 to 10 are the benzyl quaternary ammonium salts series of surfactants. Evaluation of these surfactants in the rocking cells demonstrated that they are not effective in preventing hydrate agglomeration at 40% water cut.

The n-butyl quaternary ammonium salts depicted in examples 11 and 13 were effective anti-agglomeration chemicals. They showed good performance at water cuts up to 45%. These two examples are composed of n-octyl and oleyl amides as the hydrophobic group, respectively. Surprisingly, example 12, which contains n-dodecyl amide group, failed at 40% water cut. This result is unexpected as based on prior experiences; surfactants containing n-dodecyl groups tend to be more effective than when shorter hydrophobic groups are used. However, the results from this single experiment do not necessarily mean an absolute failure because other system conditions may result in a pass for currently failed experiments, e.g. lower water cuts, different brines, different gas compositions, other crude oils.

In general, the best anti-agglomeration performance is observed for the surfactants in examples 16 to 20. These compounds present n-hexyl groups as the $R_2$ group and different alkyl amides. The most effective AA is shown in example 18 where oleyl amide is the hydrophobic group of the surfactant. This compound is effective in preventing the agglomeration of gas hydrates at water cuts as high as 60% in rocking cell experiments. Another great performer is observed in example 17 where the $R_1$ group is n-dodecyl group. This surfactant provides hydrate agglomeration inhibition at water cuts up to 55%. Example 16, which presents an n-octyl amide group, also demonstrated good performance by passing the AA test at 45% water cut. In summary, the optimum AA performance is observed for the series of surfactants containing the n-hexyl group in the $R_2$ position. Failures do not necessarily mean an absolute failure because other system conditions may result in a pass for currently failed experiments.

| Example | % Active ingredient | Dose % | Maximum Water Cut |
| --- | --- | --- | --- |
| Blank | N/A | N/A | None |
| Comparative Example A | 60 | 1.0 | 40% |
| Comparative Example B | 40 | 1.5 | 40% |
| 1 | 60 | 1.0 | <40% |
| 2 | 60 | 1.0 | <40% |
| 3 | 60 | 1.0 | 40% |
| 4 | 40 | 1.5 | Not tested yet |
| 5 | 40 | 1.5 | Not tested yet |
| 6 | 60 | 1.0 | <40% |
| 7 | 60 | 1.0 | <40% |
| 8 | 60 | 1.0 | <40% |
| 9 | 40 | 1.5 | Not tested yet |
| 10 | 40 | 1.5 | <40% |
| 11 | 60 | 1.0 | 45% |
| 12 | 60 | 1.0 | <40% |
| 13 | 60 | 1.0 | 45% |
| 14 | 40 | 1.5 | 45% |
| 15 | 40 | 1.5 | 40% |
| 16 | 60 | 1.0 | 45% |
| 17 | 60 | 1.0 | 55% |
| 18 | 60 | 1.0 | 60% |
| 19 | 40 | 1.5 | <40% |
| 20 | 40 | 1.5 | 45% |

We claim:

1. A method of inhibiting the formation of hydrate agglomerates in a fluid comprising water, gas, and optionally liquid hydrocarbon comprising adding to the fluid an effective amount of a composition comprising the following formula and optionally salts thereof:

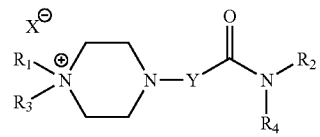

wherein $R_1$ is $C_4H_9$, $C_6H_{13}$, $C_8H_{17}$, or benzyl;
wherein $R_2$ is a $C_8H_{17}$, $C_{12}H_{25}$, or $C_{18}H_{35}$;
wherein $R_3$ is $CH_3$ or $C_2H_5$;
wherein $R_4$ is $C_nH_{2n+1}$, wherein n=0 to 22; or H
wherein $X^-$ is an anion, halogen, a carboxylate, or a sulfate and wherein $X^-$ is only present when both $R_1$ and $R_3$ are present; and
wherein $Y=(CH_2)_n$, wherein n=1 to 8.

2. The method of claim 1, wherein $R_1$ and/or $R_2$ and/or $R_4$ are linear, branched, and/or cyclic.

3. The method of claim 1, wherein the halogen is selected from chlorine, bromine, iodine, or combinations thereof.

4. The method of claim 1, wherein $Y=(CH_2)_n$, wherein n=1 to 4.

5. The method of claim 1, where $Y=(CH_2)_n$, wherein n=1 to 2.

6. The method of claim 1, comprising the following formula and optionally salts thereof:

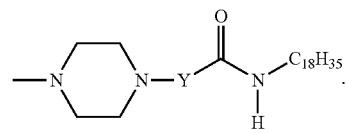

7. The method of claim 1, comprising the following formula:

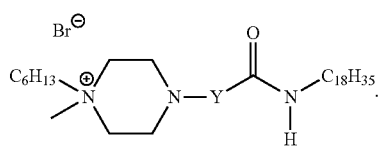

8. The method of claim 1, wherein the composition further comprises one or more hydrate inhibitors.

9. The method of claim 1, wherein the composition further comprises one or more thermodynamic hydrate inhibitors, one or more kinetic hydrate inhibitors, one or more anti-agglomerates, or a combination thereof.

10. The method of claim 1, wherein the composition further comprises one or more asphaltene inhibitors, paraffin inhibitors, corrosion inhibitors, scale inhibitors, emulsifiers, water clarifiers, dispersants, emulsion breakers, or a combination thereof.

11. The method of claim 1, wherein the composition further comprises one or more polar or nonpolar solvents or a mixture thereof.

12. The method of claim 1, wherein the composition further comprises one or more solvents selected from isopropanol, methanol, ethanol, heavy aromatic naptha, toluene, ethylene glycol, ethylene glycol monobutyl ether (EGMBE), diethylene glycol monoethyl ether, xylene, kerosene, diesel, isobutanol, heptane, or a combination thereof.

13. The method of claim 1, wherein $R_2$ and $R_4$ are independently linear, branched, and/or cyclic.

14. The method of claim 1, wherein $Y=(CH_2)_n$, wherein n=1 to 4.

15. The method of claim 1, wherein said fluid has a salinity of 1 to 20 w/w percent total dissolved solids.

16. The method of claim 1, wherein said fluid has a water cut from 1 to 60 v/v percent.

17. The method of claim 1, wherein the fluid is contained in an oil or gas pipeline.

18. A method of inhibiting the formation of hydrate agglomerates in a fluid comprising water, gas, and optionally liquid hydrocarbon comprising adding to the fluid an effective amount of a composition produced by reacting an alkyl acrylate with 1-methylpiperazine and then subsequently reacting the resulting product with an amine to form an amide and reacting said amide with an alkyl halide.

19. The composition of claim 18, wherein said amine is oleylamine.

20. The composition of claim 18, wherein the alkyl halide is a 1-bromohexane.

21. A composition comprising the following formula and optionally salts thereof:

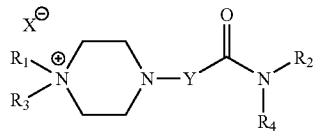

wherein $R_1$ is $C_4H_9$, $C_6H_{13}$, $C_8H_{17}$, or benzyl;
wherein $R_2$ is a $C_8H_{17}$, $C_{12}H_{25}$, or $C_{18}H_{35}$;
wherein $R_3$ is $CH_3$ or $C_2H_5$;
wherein $R_4$ is $C_nH_{2n+1}$, wherein n=0 to 22; or H
wherein $X^-$ is an anion, halogen, a carboxylate, or a sulfate and wherein $X^-$ is only present when both $R_1$ and $R_3$ are present; and
wherein $Y=(CH_2)_n$, wherein n=1 to 8.

* * * * *